United States Patent [19] [11] 4,150,167
Mathias et al. [45] Apr. 17, 1979

[54] METHOD OF COATING WITH POLYENES DERIVED FROM HYDANTOIN ACIDS, AMINES AND ESTERS

[75] Inventors: Eckart Mathias, Catonsville; Charles R. Morgan, Brookeville, both of Md.

[73] Assignee: W. R. Grace & Co., New York, N.Y.

[21] Appl. No.: 835,397

[22] Filed: Sep. 21, 1977

Related U.S. Application Data

[62] Division of Ser. No. 697,284, Jun. 17, 1976, Pat. No. 4,084,020.

[51] Int. Cl.$^2$ .............................................. B05D 3/06
[52] U.S. Cl. ................................ 427/44; 204/159.14; 427/54
[58] Field of Search ................... 204/159.14, 159.15, 204/159.16, 159.18, 159.19; 427/44, 54, 41

[56] References Cited

U.S. PATENT DOCUMENTS

| | | | |
|---|---|---|---|
| 3,976,553 | 8/1976 | Larsen | 204/159.22 |
| 3,984,297 | 10/1976 | Morgan | 204/159.22 |
| 3,984,606 | 10/1972 | Morgan | 428/419 |

*Primary Examiner*—John H. Newsome
*Attorney, Agent, or Firm*—Richard P. Plunkett; William W. McDowell, Jr.

[57] ABSTRACT

This invention is directed to polyenes derived from hydantoin acids, amines and esters. The polyene is typically a reaction product of a hydantoin amine, e.g., N,N'-bis(3-aminopropyl)-dimethylhydantoin, a diisocyanate and an unsaturated ether, e.g., trimethylolpropane diallyl ether. Upon exposure to a free radical generator, e.g., actinic radiation, in combination with a polythiol, this polyene cures to a solid, insoluble, chemically resistant, crosslinked polythioether product having excellent heat stability.

2 Claims, No Drawings

METHOD OF COATING WITH POLYENES DERIVED FROM HYDANTOIN ACIDS, AMINES AND ESTERS

This is a division of application Ser. No. 697,284 filed June 17, 1976 U.S. Pat. No. 4,084,020.

This invention relates to polyenes prepared from hydantoin acids, amines and esters.

One object of the instant invention is to prepare novel polyenes from hydantoin acids, amines and esters. Another object of the instant invention is to prepare polyenes from hydantoin acids, amines and esters which upon curing with polythiols result in cured polythioethers having excellent heat stability. Other objects will become apparent from a reading hereinafter.

Generally speaking, the invention herein is a polyene of the formula:

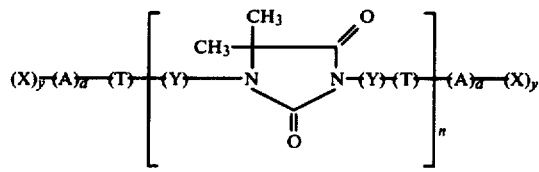

wherein Y is alkylene containing 2 to 3 carbon atoms; T is a member of the group consisting of

A is a polyvalent organic radical member free of reactive carbon to carbon unsaturation and independently selected from the group consisting of aryl, substituted aryl, aralkyl, substituted aralkyl, cycloalkyl, substituted cycloalkyl, alkyl and substituted alkyl each containing up to 36 carbon atoms and mixtures thereof, said group members can be connected by a chemically compatible linkage selected from the group consisting of —O—, —S—, carboxylate, carbonate, carbonyl, urethane and substituted urethane, urea and substituted urea, amide and substituted amide, amine and substituted amine, and sulfone; said substituents on the substituted members may be such groups as chloro, bromo, nitro, acetoxy, acetamido, phenyl, benzyl, alkyl and alkoxy of 1 to 9 carbon atoms, and cycloalkyl of 3 to 8 carbon atoms, X is a member selected from the group consisting of (a) —(CH$_2$)$_d$—CR'=CHR, (b) —O—(CH$_2$)$_d$—CR'=CHR, (c) —S—(CH$_2$)$_d$—CR'=CHR, (d) —(CH$_2$)$_d$—C≡CR, (e) —O—(CH$_2$)$_d$—C≡CR, (f) —S—(CH$_2$)$_d$—C≡CR;

and mixtures thereof; where R and R' each are independently selected from the group consisting of hydrogen and methyl radicals; d is an integer from 0 to 1; n is 1 to 30; and y from 1 to 10.

The formation of such polyenes may be schematically represented by the following non-limiting equations. For example, an amidation reaction can be carried out between hydantoin-containing acid, e.g., N,N'-bis(2-carboxyethyl)-dimethylhydantoin and an amine, e.g., diallyl amine to form a hydantoin containing polyene thusly.

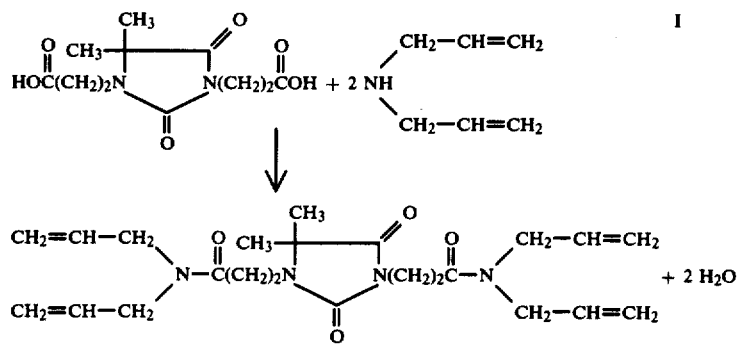

The same hydantoin containing acid can be reacted with an isocyanate, e.g., isophorone diisocyanate capped with an alcohol on one of the isocyanate groups, e.g., trimethylolpropane diallyl ether thusly:

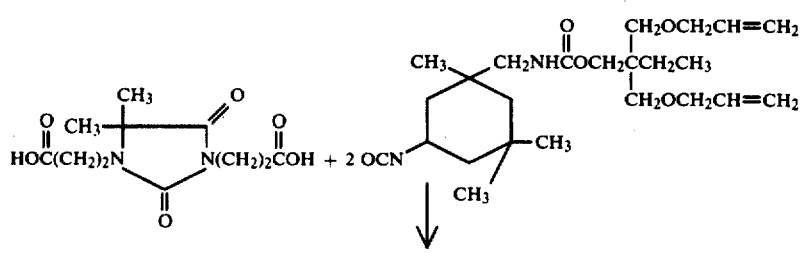

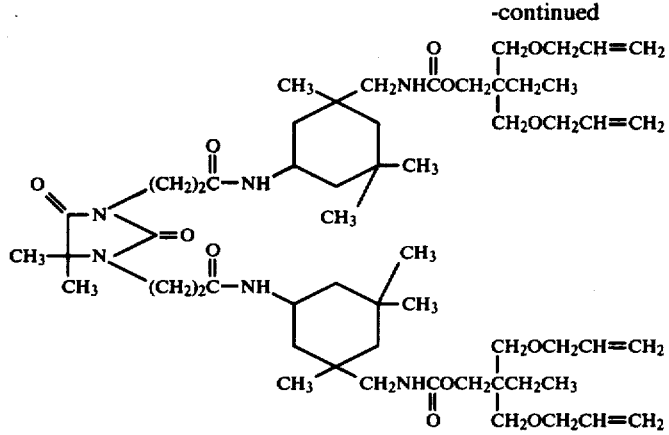

$+ 2 CO_2$

Polyenes can also be formed using a hydantoin containing amine, e.g., N,N'-bis(3-aminopropyl)-dimethylhydantoin with an unsaturated acid, e.g., acrylic acid thusly:

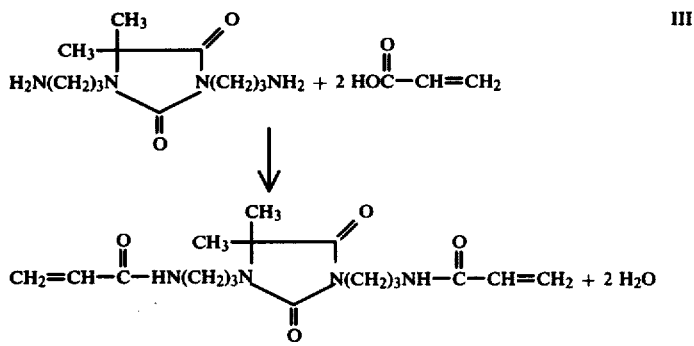

III

Still another reaction with the amine is that wherein a sulfonyl containing compound, e.g., diphenyl ether 4,4'-disulfonyl chloride is end-capped with an unsaturated compound, e.g., allyl alcohol thusly:

and then reacted stoichiometrically with a hydantoin containing amine, e.g., N,N'-bis(3-aminopropyl)-dimethylhydantoin to form a hydantoin containing polyene:

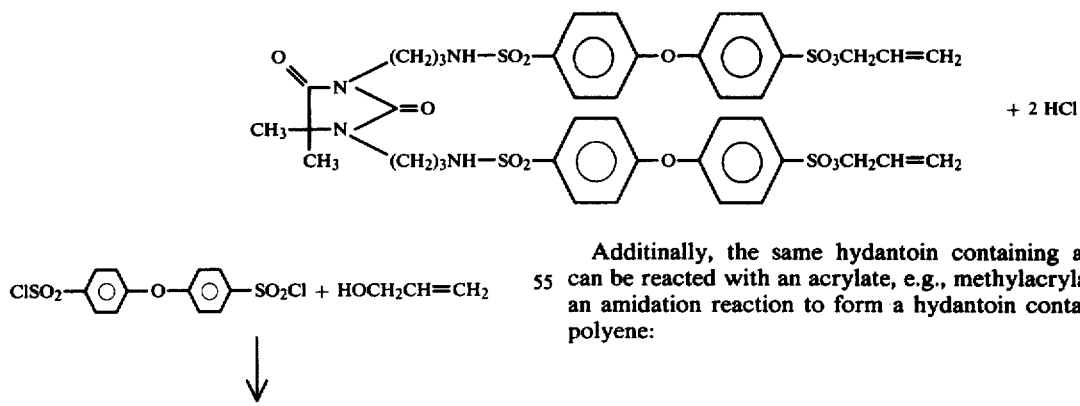

$+ 2 HCl$

Additionally, the same hydantoin containing amine can be reacted with an acrylate, e.g., methylacrylate in an amidation reaction to form a hydantoin containing polyene:

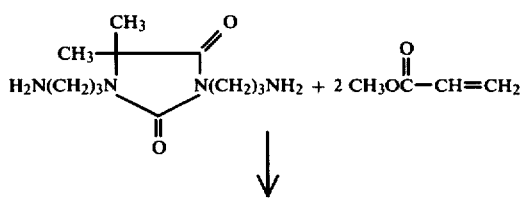

V

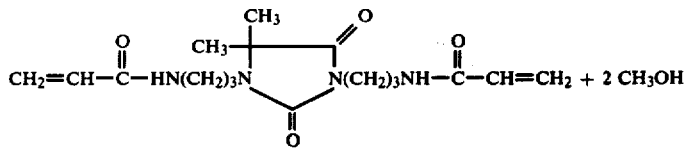

Still another method of forming a hydantoin containing polyene is by transesterification between a hydantoin containing ester, e.g., dimethylester of N,N-bis(2-carboxyethyl)-dimethylhydantoin and an alcohol, e.g., allyl alcohol thusly:

Similarly, a hydroxy-terminated hydantoin containing polymeric unit can be made by treating, e.g., n of the hydantoin containing acid, e.g., N,N'-bis(2-carboxyethyldimethylhydantoin, with n+1 of a diol, e.g., same as above.

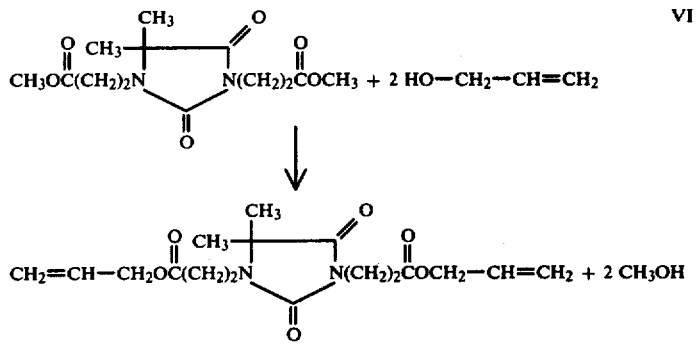

VI

By the practice of the instant invention it is also possible to make polyenes with recurring hydantoin containing polymeric units. One method of carrying this out would be to react n+1 of a hydantoin containing acid, e.g., N,N'-bis(2-carboxyethyl)-dimethylhydantoin with n of a diol, e.g., ethylene glycol to form the following carboxy-terminated polymeric unit;

The resultant hydroxy and acid terminated polymeric material can then be capped with various reactants such as trimethylolpropane diallyl ether, diallyl amine, an ene-capped isocyanate having one free isocyanae group, hydroxypropylacrylate and hydroxyethylacrylate. Herein, for examplification, hydroxyethylacrylate is used.

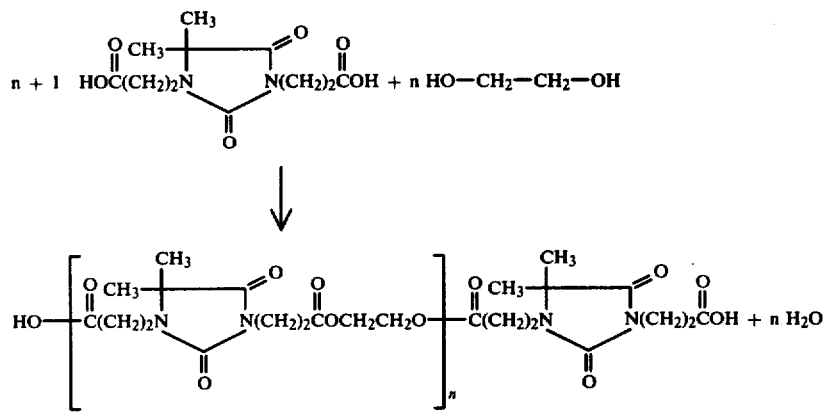

VII

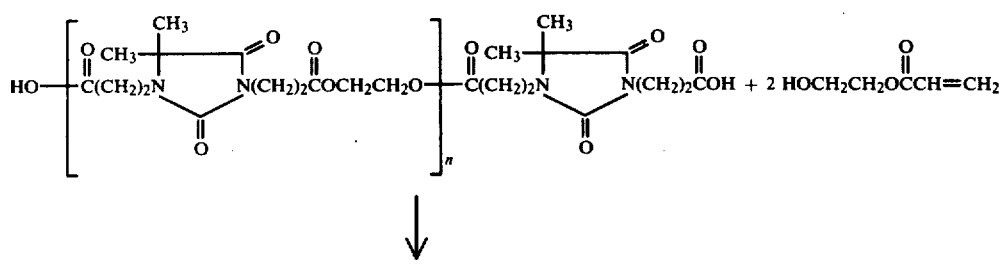

VIII

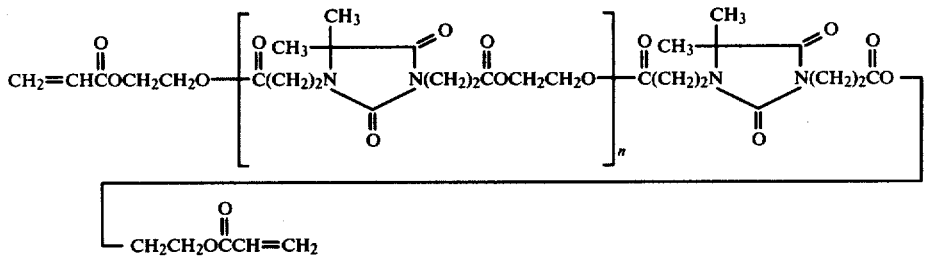

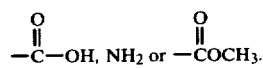

Additionally, polymeric hydantoin containing polyene can also be formed from a hydantoin containing acid, e.g., N,N'-bis(2-carboxyethyl)-dimethylhydantoin and hydantoin containing amine, e.g., N,N'-bis(3-aminopropyl)-dimethylhydantoin and then capped with the same unsaturated groups to from a polyene as set out above.

It is also possible by the instant invention to form polymeric hydantoin containing materials by reacting a hydantoin containing amine, e.g., N,N'-bis(3-aminopropyl)-dimethylhydantoin with a diisocyanate, e.g., toluene diisocyanate in substantially equal mole amounts to get a chain-extended polymeric material which can be then capped to produce the ene unsaturation by the materials set out supra.

It is also possible to react a hydantoin containing amine and a hydantoin containing ester to form repeating polymeric units and, thereafter, cap these units with ethylenically unsaturated materials. Another method of forming polymeric hydantoin polyenes is to react a hydantoin containing polyester, e.g., dimethylester of N,N'-bis(2-carboxyethyl)-dimethylhydantoin with a diol, e.g., butylene glycol and, thereafter, cap the resultant repeating units with various unsaturated materials including those set out supra. In forming the polymeric hydantoin containing materials herein, the number of repeating units is usually in the range 2 to 30.

The hydantoin based acids, amines and esters herein can be represented by the general formula:

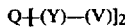

wherein
Q is

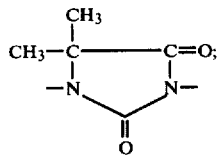

Y is an alkylene containing 2 to 3 carbon atoms and V is $$-\overset{O}{\underset{\|}{C}}-OH, \ NH_2 \ or \ -\overset{O}{\underset{\|}{C}}OCH_3.$$

One group of operable polyenes containing a hydantoin backbone is of unsaturated ureas formed by the reactions of N,N'-bis(3-aminopropyl)-dimethylhydantoin with a polyene isocyanate.

Polyenes thus made may be represented by the general formula:

wherein
Q, Y, A and X are as hereinbefore set forth,
T is the member $$-\overset{O}{\underset{\|}{N}}HCNH-,$$

d is 1, and y is from 1 to 10.

A further group of operable polyenes containing a hydantoin backbone are polyamides formed by reacting the N,N'-bis(3-aminopropyl)-dimethylhydantoin with the dimethylester of the N,N'-bis(2-carboxyethyl)-dimethylhydantoin. The polyamide thus formed is subsequently capped with a polyene isocyanate. Polymeric polyenes thus made are represented by the general formula:

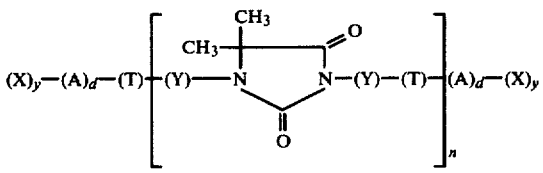

where Q and Y are as hereinbefore set forth, T is the member $$-\overset{O}{\underset{\|}{C}}NH- \ \text{and} \ -\overset{O}{\underset{\|}{N}}HCNH-;$$

A, X, d and y are as hereinbefore set forth; and n is an integer from 1 to 30.

As used herein, polyenes and polyynes refer to simple or complex species of alkenes or alkynes having a multiplicity of pendant or terminally reactive carbon to carbon unsaturated functional groups per average molecule. For example, a diene is a polyene that has two reactive carbon to carbon double bonds per average molecule, while a diyne is a polyyne that contains two reactive carbon to carbon triple bonds per average molecule. For purposes of brevity, all these classes of compounds will be referred to hereafter as polyenes.

In defining the position of the reactive functional carbon to carbon unsaturation, the term terminal is intended to mean that functional unsaturation is at an end of the main chain in the molecule. The term pendant means that the reactive carbon to carbon unsaturation is located terminal in a branch of the main chain as contrasted to a position at or near the ends of the main chain. For purposes of brevity, all of these positions are referred to herein generally as terminal unsaturation.

Functionality as used herein refers to the average number of ene or thiol groups per molecule in the polyene or polythiol, respectively. For example, a triene is a polyene with an average of three reactive carbon to carbon unsaturated groups per molecule, and thus has a functionality (f) of three. A dithiol is a polythiol with an average of two thiol groups per molecule and thus has a functionality (f) of two.

The term reactive unsaturated carbon to carbon groups means groups which will react under proper conditions as set forth herein with thiol groups to yield the thioether linkage

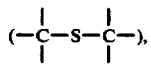

as contrasted to the term unreactive carbon to carbon unsaturation which means

groups found in aromatic nuclei (cyclic structures exemplified by benzene, pyridine, anthracene, and the like) which do not under the same conditions react with thiols to give thioether linkages. For purposes of brevity, this term will hereinafter be referred to generally as reactive unsaturation or a reactive unsaturated compound.

As used herein, the term polyvalent means having a valence of two or greater.

The term reactive unsaturated isocyanate will hereinafter be referred to as an ene-isocyanate or an yne-isocyanate.

To make the polyamide polyene, the reaction is carried out under vacuum at a temperature range of 40° to 100° C. while the byproduct, methanol, is continuously pumped off. The reagents are added in a 1:1 mole ratio. The reaction, if desired, may be carried out in the presence of a catalyst. Prior to adding the capping compound, a small amount of the diamine is added to insure that the polymer has amine end groups. The unsaturated isocyanates are then added to the polyamide melt and kept at 100° to 140° C. for a few minutes.

The reactive unsaturated isocyanates are a group of compounds having the general formula $$OCN—(A)_d—(X)_y$$

in which the members A and X and the integers d and y are as hereinbefore set forth, and OCN is isocyanate.

Other operable ene- or yne-isocyanates are those prepared by reacting a polyisocyanate of the general formula A—(NCO)$_x$, in which x is at least 2 and A is as hereinbefore set forth; with a reactive unsaturated alcohol of the general formula $(X)_y—(A)_d—OH$ or a reactive unsaturated amine of the formula $(X)_y—(A)_d—NH_2$ or $[(X)_y—(A)_d]_2—NH$ in which X, A, y and d are as hereinbefore set forth.

Operable non-limiting examples of starting polyisocyanate reactants include hexamethylenediisocyanate, tolylene diisocyanate, xylylene diisocyanate, methylenebis(phenyl isocyanate), 4,4'-methylene(cyclohexyl isocyanate), 1-methoxy-2,4,6-benzene-triisocyanate, 2,4,4'-triisocyanatodiphenylether, diphenylmethane tetraisocyanates, polyisocyanates having various functional groups such as N,N',N''-tri(isocyanatohexyl)-biuret or adducts of polyalcohols and diisocyanates which have at least 2 free isocyanate groups. Adduct of trimethylolpropane and 3 moles of toluene diisocyanate, is suitable.

Illustrative of the operable reactive unsaturated alcohols which may react with the polyisocyanates to give the desired ene-isocyanate include but are not limited to allyl and methallyl alcohol, crotyl alcohol, crotyl alcohol, ω-undecylenyl alcohol, 2-vinyloxyethanol, vinylhydroxyethyl sulfide, propargyl alcohol, 1-allylcyclopentanol, 2-methyl-3-butene-2-ol. Reactive unsaturated derivatives of polyhydric alcohols such as glycols, triols, tetraols, etc. are also suitable. Representative examples include trimethylolpropane or trimethylolethane diallyl ethers, pentaerythritol triallyl ether and the like. Mixtures of various reactive unsaturated alcohols are operable as well. A suitable ene-isocyanate is prepared by treating one mole of trimethylbenzene triisocyanate with two moles of trimethylolpropane diallyl ether. The resulting urethane containing ene-isocyanate is a polyene having four reactive allyl ether groups per molecule. Mixtures of various ene- or yne-isocyanates are operable as well.

Operable non-limiting examples of reactive unsaturated amines are allyl amine, diallylamine, allylcyclohexylamine, which may also be reacted with polyisocyanates to give the desired ene-isocyanate. Mixtures of various reactive unsaturted amines are also operable.

Illustrative of the operable non-limiting examples of polyamines to give the desired amides include hexamethylene diamine, tolylene diamine, xylylene diamine, methylene dianiline, 4,4'-methylene (cyclohexyl diamine), 1-methoxy-2,4,6-benzene triamine, 2,4,4'-triaminodiphenylether, diphenylmethane tetra-amine, polyamines having various functional groups such as N,N',N'-tris-(aminohexyl)-biuret or adducts of polyamines and diisocyanates which have at least 2 free isocyanate groups.

Another class of polyenes operable in forming the curable polyene-polythiol system of th subject invention are esters of N,N'-bis(2-carboxyethyl)-dimethylhydantoin. Similarly these polyenes may be represented by the general formula:

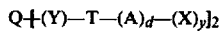

where T is the

group whose carbonyl arises from the hydantoin derived diacid, the members Q, Y, A, X and integers d and y are as hereinbefore set forth.

A general method of forming these esters is to react the hydantoin diacid with two moles of one or more types of alcohols given by the general formula $(X)_y—(A)_d—OH$ in which the members X and A and the integers y and d are as hereinbefore set forth.

The esterification reaction may be carried out in a conventional manner in the presence of an acid catalyst, the water formed during the reaction being removed as an azeotrope. The reaction is carried out at atmospheric pressure at a temperature in the range of from 60° to about 150° C., pereferably from 60° to 110° C., for a period of 30 minutes to about 24 hours. Suitable acid catalysts include but are not limited to p-toluenesulfonic acid, sulfuric acid, methanesulfonic acid and the like. Useful inert solvents include but are not limited to saturated aliphatic hydrocarbons, ethers, ketones, etc. Representative non-limiting examples of solvents include toluene, benzene, xylene, chloroform, 1.2-dichloroethane, etc.

In summary, by admixing the novel hydantoin based polyenes with polythiols and, thereafter, exposing the mixture at ambient conditions to a free radical generator, a solid, cured insoluble polythioether product having a high percent elongation is obtained.

As used herein, the term polythiols refers to simple or complex organic compounds having a multiplicity of pendant or terminally positioned —SH functional groups per average molecule.

On the average the polythiols must contain 2 or more —SH groups/molecule and usually have a viscosity range of slightly above 0 to 20 million centipoises (cps) at 70° C., as measured by a Brookfield Viscometer. Included in the term "polythiols" as used herein are those materials which in the presence of an inert solvent, aqueous dispersion of plasticizer fall within the viscosity range set out above at 70° C. Operable polythiols in the instant invention usually have molecular weights in the range 94–20,000, preferably 100–10,000.

The polythiols operable in the instant invention can be exemplified by the general formula: $R_8$—$(SH)_n$ where n is at least 2 and $R_8$ is a polyvalent organic moiety free from reactive carbon to carbon unsaturation. Thus $R_8$ may contain cyclic groupings and minor amounts of hetero atoms such as N, S, P or O but primarily contains carbon-hydrogen, carbon-oxygen, or silicon-oxygen containing chain linkages free of any reactive carbon to carbon unsaturation.

One class of polythiols operable with polyenes in the instant invention to obtain essentially odorless polythioether products are esters of thiol-containing acids of the general formula HS—$R_9$—COOH, where $R_9$ is an organic moiety containing no "reactive" carbon to carbon unsaturation, with polyhydroxy compounds of the general structure $R_{10}$—$(OH)_n$, where $R_{10}$ is an organic moiety containing no "reactive" carbon to carbon unsaturation and n is 2 or greater. These components will react under suitable conditions to give a polythiol having the general structure

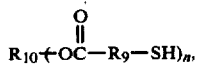

wherein $R_9$ and $R_{10}$ are organic moieties containing no "reactive" carbon to carbon unsaturation and n is 2 or greater.

Certain polythiols such as the aliphatic monomeric polythiols (ethane dithiol, hexamethylene dithiol, decamethylene dithiol, tolylene-2,4-dithiol, etc. and some polymeric polythiols such as a thiol-terminated ethylcyclohexyl dimercaptan polymer, etc. and similar polythiols which are conveniently and ordinarily synthesized on a commercial basis, although having obnoxious odors, are operable in this invention but many of the end products are not widely accepted from a practical, commercial point of view. Examples of the polythiol compounds preferred for this invention because of their relatively low odor level include but are not limited to esters of thiogylcolic acid (HS—$CH_2$COOH), α-mercaptopropionic acid (HS—CH($CH_3$)—COOH) and β-mercaptopropionic acid (HS—$CH_2CH_2$COCH) with polyhydroxy compounds such as glycols, triols, tetraols, pentaols, hexaols, etc. Specific examples of the preferred polythiols include but are not limited to ethylene glycol bis (thioglycolate), ethylene glycol bis (β-mercaptopropionate), trimethylolpropane tris (thioglycolate), trimethylolpropane tris (β-mercaptopropionate), pentaerythritol tetrakis (thioglycolate) and pentaerythritol tetrakis (β-mercaptopropionate), all of which are commercially available. A specific example of a preferred polymeric polythiol is polypropylene ether glycol bis (β-mercaptopropionate) which is prepared from polypropylene-ether glycol (e.g. Pluracol P2010, Wyandotte Chemical Corp.) and β-mercaptopropionic acid by esterification.

Additionally, polythiols operable herein to give cured solid polythioether products with the hydantoin containing polyene in the presence of a free radical generator include the mercaptoester derivatives of styrene-allyl alcohol copolymers set out in U.S. Pat. No. 3,904,499 and the isocyanurate containing polythiols disclosed in U.S. Pat. No. 3,676,440 both incorporated herein by reference.

The preferred polythiol compounds are characterized by a low level of mercaptan-like odor initially, and after reaction, give essentially odorless polythioether end products which are commercially attractive and practically useful resins or elastomers for both indoor and outdoor applications.

Prior to curing, the polyene and polythiol components are admixed in a suitable manner so as to form a homogeneous liquid curable mixture. Thus, the polyene and polythiol reactants can be admixed without the necessity of using a solvent a room temperature or slightly elevated temperatures up to about 80° C. when one of the components is a solid or, if desired, the reactants may be dissolved in a suitable solvent and thereafter the solvent can be removed by suitable means such as evaporation.

To obtain the maximum strength, solvent resistance, creep resistance, heat resistance and freedom from tackiness, the reactive components consisting of the polyenes and polythiols are formulated in such a manner as to give solid, crosslinked, three dimensional network polythioether polymer systems on curing. In order to achieve such infinite network formation, the individual polyenes and polythiols must each have a functionality of at least 2 and the sum of the functionalities of the polyene and polythiol components must always be greater than 4. Blends and mixtures of various polyenes and various polythiols containing said functionality are also operable herein.

The compositions to be cured in accord with the present invention may, if desired, include such additives as antioxidants, accelerators, dyes, inhibitors, activators, fillers, thickeners, pigments, anti-static agents, flame-retardant agents, surface-active agents, extending oils, plasticizers and the like within the scope of this invention. Such additives are usually pre-blended with the polyene or polythiol prior to or during the compounding step. The aforesaid additives may be present in quantities up to 500 or more parts based on 100 parts by weight of the polyene-polythiol curable compositions and preferably 0.005–300 parts on the same basis.

The polythioether-forming components and compositions, prior to curing may be admixed with or blended with other monomeric and polymeric materials such as thermoplastic resins, elastomers or thermosetting resin monomeric or polymeric compositions. The resulting blend may be subjected to conditions for curing or co-curing of the various components of the blend to give cured products having unusual physical properties.

Although the mechanism of the curing reaction is not completely understood, it appears most likely that the curing reaction may be initiated by most any free radical generating source which dissociates or abstracts a hydrogen atom from an SH group, or accomplishes the equivalent thereof. Generally, the rate of the curing reaction may be increased by increasing the temperature of the composition at the time of initiation of cure. In most applications, however, the curing is accomplished conveniently and economically by operating at ordinary room temperature conditions.

Operable curing initiators or accelerators include radiation such as actinic radiation, e.g., ultraviolet light, lasers; ionizing radiation such as gamma radiation, x-rays, corona discharge, etc.; as well as chemical free radical generating compounds such as azo, peroxidic, benzopinacol, etc., compounds.

Azo, benzopinacoles or peroxidic compounds (with or without amine accelerators) which decompose at ambient or slightly elevated temperature conditions are operable as free radical generating agents capable of accelerating the curing reaction include benzoyl peroxide, di-t-butyl peroxide, cyclohexanone peroxide with dimethyl aniline or cobalt naphthenate as an accelerator; hydroperoxides such as hydrogen peroxide, cumene hydroperoxide, t-butyl hydroperoxides; peracid compounds such as t-butylperbenzoate, peracetic acid; persulfates, e.g., ammonium persulfate; azo compounds such as azobis-isobutyronitrile and the like.

These free radical generating agents are usually added in amounts ranging from about 0.001 to 10 percent by weight of the curable solid polyene-polythiol composition, preferably .01 to 5 percent.

The curing period may be retarded or accelerated from less than 1 minute to 30 days or more.

Conventional curing inhibitors or retarders which may be used in order to stabilize the components or curable compositions so as to prevent premature onset of curing may include hydroquinone; p-tert-butyl catechol; 2,6-di tert-butyl-p-methylphenol; phenothiazine; N-phenyl-2-naphthylamine; phosphorous acid; pyrogallol and the like.

The preferred free radical generator for the curing reaction is actinic radiation, suitably in the wavelength of about 2000 to 7500 Å, preferably for 2000 to 4000 Å.

A class of actinic light useful herein is ultraviolet light, and other forms of actinic radiation which are normally found in radiation emitted from the sun or from artificial sources such as Type RS Sunlamps, carbon arc lamps, xenon arc lamps, mercury vapor lamps, tungsten halide lamps and the like. Ultraviolet radiation may be used most efficiently if the photocurable polyene/polythiol composition contains a suitable photocuring rate accelerator. Curing periods may be adjusted to be very short and hence commercially economical by proper choice of ultraviolet source, photocuring rate accelerator and concentration thereof, temperature and molecular weight, and reactive group functionality of the polyene and polythiol. Curing periods of less than about 1 second duration are possible, especially in thin film applications such as desired, for example, in coatings, adhesives and photoimaged surfaces.

Various photosensitizers, i.e., photocuring rate accelerators are operable and well known to those skilled in the art. Examples of photosensitizers include, but are not limited to, benzophenone o-methoxybenzophenone, acetophenone, o-methoxyacetophenone, acenaphthenequinone, methyl ethyl ketone, valerophenone, hexanophenone, γ-phenylbutyrophenone, p-morpholinopropiophenone, dibenzosuberone, 4-morpholinobenzophenone, benzoin, benzoin methyl ether, 4'-morpholinodeoxybenzoin, p-diacetylbenzene, 4-aminobenzophenone, 4'-methoxyacetophenone, benzaldehyde, o-methoxybenzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,5-triacetylbenzene, thioxanthen-9-one, xanthene-9-one, 7-H-benz[de]anthracen-7-one, 1-naphthaldehyde, 4,4'-bis(dimethylamino)benzophenone, fluorene-9-one, 1'-acetonaphthone, 2'-acetonaphthone, triphenylphosphine, tri-o-tolylphosphine, acetonaphthone and 2,3-butanedione, benz[a]anthracene 7,12 dione, benzoin isopropyl ether, benzoin isobutyl ether, benzoin ethyl ether, diethoxyacetophenone, 2,2-dimethoxy-2-phenylacetophenone, benzoin tetrahydropyranyl ether, etc., which serve to give greatly reduced exposure times and thereby when used in conjunction with various forms of energetic radiation yield very rapid, commercially practical time cycles by the practice of the instant invention.

These photocuring rate accelerators may range from about 0.005 to 50 percent by weight of the photocurable polyenepolythiol composition, preferably 0.05 to 25 percent.

The mole ratio of the ene/thiol groups for preparing the curable composition is from about 0.2/1.0 to about 8/1.0, and preferably from 0.5/1.0 to about 2/1.0 group ratio.

The curable hydantoin based polyenes with various polythiols are used in preparing solid, cured crosslinked insoluble polythioether polymeric products having many and varied uses, examples of which include, but are not limited to, coatings; adhesives; films; molded articles; imaged surfaces, e.g., solid photoresists; solid printing plates; e.g., offset, lithographic, letterpress, gravures, etc., silverless photographic materials and the like.

Since the cured materials formed from the polyenepolythiol composition possess various desirable properties such as resistance to adverse chemical and physical environments, and have a high percent elongation, they are particularly useful for preparing coatings.

A general method for preparing coatings, comprises coating the curable compositions on a solid surface of a substrate such as plastic, rubber, glass, e.g., optical fibers, ceramic, metal, e.g., wire, paper and the like; exposing directly to radiation, e.g., U.V. light, until the curable composition cures and crosslinks in the exposed areas.

It is to be understood, however, that when energy sources, e.g., ionizing radiation, other than visible or ultraviolet light, are used to initiate the curing reaction, photocuring rate accelerators (i.e., photosensitizers, etc.) generally are not required in the formulation.

When U.V. radiation is used for the curing reaction, a dose of 0.0004 to 6.0 watts/cm$^2$ is usually employed.

The following examples are set out to describe, but expressly not limit, the instant invention. Unless otherwise noted, all parts and percentages are by weight. The measurements for modulus, tensile strength and elongation to failure were measured in accordance to the ASTM D 638 test with a 50% rate of strain.

EXAMPLE 1

To a 4-necked, 1 l round bottom flask equipped with stirrer, addition funnel, thermometer, Dean-Stark trap, and reflux condenser was charged under a nitrogen blanket 77.26 g of N,N'-bis(2-carboxyethyl)-dimethylhydantoin, 4.54 g of p-toluene sulfonic acid as catalyst and 300 ml of benzene. The mixture was refluxed until the Dean-Stark trap was full of benzene, and then 36.26 g of allyl alcohol in 50 ml of benzene was added during a period of 35 minutes. When no more water was azeotroping into the Dean-Stark trap, the heat was turned off and the product was worked up by washing it twice with 150 ml of water, then twice with 100 ml of 5% aq. NaHCO₃, and then again twice with 100 ml of water. The benzene layer containing the product was then dried with anhydrous MgSO₄, treated with decolorizing carbon, and then distilled under vacuum until all the benzene was taken off. The clear syrupy product, i.e.,

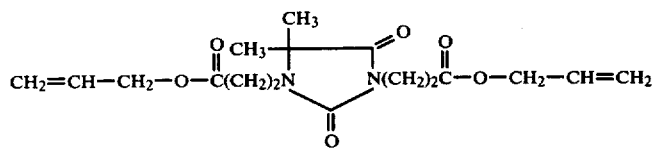

showed a C═C analysis of 5.65 mmoles/g.

EXAMPLE 2

Example 1 was repeated except that in place of the allyl alcohol, 70.92 g of trimethylolpropane diallyl ether was added to 40.95 g of N,N'-bis(2-carboxyethyl)dimethylhydantoin with 4.47 g of p-toluene sulfonic acid catalyst in benzene. The product, i.e.,

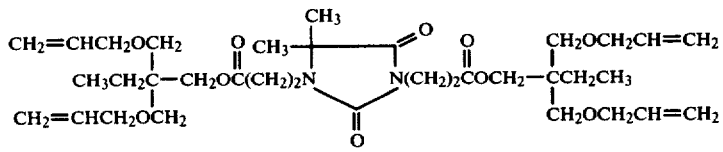

had a C═C content of 6.04 mmoles/g.

EXAMPLE 3

Example 1 was repeated except that instead of allyl alcohol alone a mixture of 3.50 g of allyl alcohol and 12.91 g of trimethylolpropane diallyl ether was added to 16.00 g of N,N'-bis(2-carboxyethyl)-dimethylhydantoin with 1.30 g of p-toluene sulfonic acid catalyst in benzene. The product, i.e.,

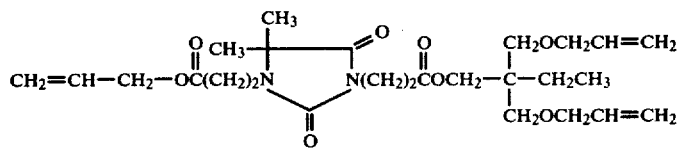

had a C═C content of 5.80 mmoles/g.

EXAMPLE 4

To a resin kettle equipped with stirrer, thermometer, and under a nitrogen blanket, was charged 365.76 g of tolylene diisocyanate. 450.01 g of trimethylolpropane diallyl ether was charged to an addition funnel and, thereafter, added dropwise to the resin kettle while maintaining the temperature below 36° C. After the addition was complete, the material was stirred overnight. The product had an NCO content of 2.42 meq/g.

To a round bottom flask, equipped with stirrer, thermometer, addition funnel and reflux condenser was charged under a nitrogen blanket, 30.03 g of the reaction product of the tolylene diisocyanate and the trimethyolpropane diallyl ether reaction, and 50 ml of ethylene dichloride. A solution of 9.21 g of N,N'-bis(3-aminopropyl)-dimethylhydantoin in 50 ml of ethylene dichloride was charged to the addition funnel and, thereafter, added dropwise into the reaction flask. The reaction mixture was left stirring overnight, after which time it was stripped of its solvent, and the reaction product, i.e.,

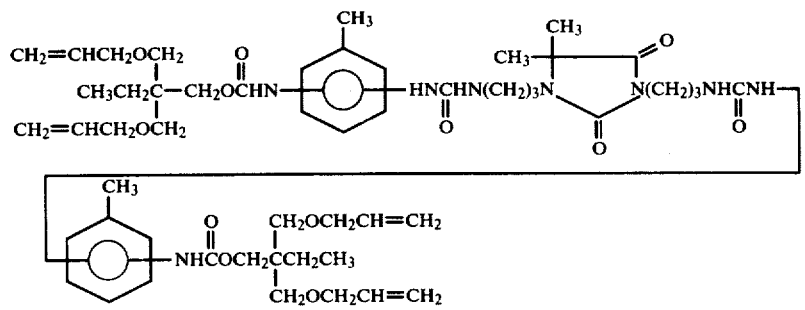

was recovered.

EXAMPLE 5

To a round bottom flask was charged 26.3 g of dimethylester of the N,N'-bis(2-carboxyethyl)-dimethylhydantoin and 10.5 g of allyl amine. The reaction mixture was left standing in an oven at 42° C. and stirred occasionally. After seven and a half days, the excess allyl amine was stripped off under vacuum. The very viscous orange colored product, i.e.,

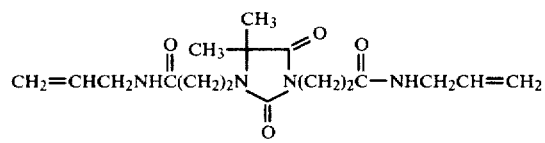

had a C=C content of 4.90 mmoles/g.

EXAMPLE 6

To a 2-liter, 3-necked round bottom flask equipped with stirrer, thermometer, Dean-Stark trap and condenser was charged 350 grams of N,N'-bis(2-carboxyethyl)dimethylhydantoin, 351.5 grams of 2-hydroxypropyl acrylate, 0.07 grams hydroquinone stabilizer, 28 grams of p-toluenesulfonic acid as a catalyst and 600 ml benzene. The mixture was refluxed until all the water was collected. The flask was cooled to room temperature and the contents were washed once with 700 ml water and twice with a 5% $NaHCO_3$ solution followed by an additional 700 ml water wash. The benzene layer containing the product was then dried with anhydrous $MgSO_4$, treated with decolorizing carbon and then benzene was removed under vacuum. The yellow low viscosity liquid product, i.e.,

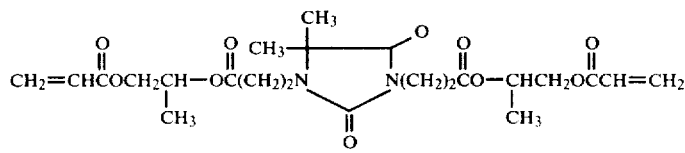

weighed 375 grams and contained 0.03 meq. H+/gm.

EXAMPLE 7

To a 2-liter, 3-necked round bottom flask equipped with stirrer, thermometer, Dean-Stark trap and condenser was charged 136.1 grams of N,N'-bis(2-carboxyethyl)-dimethylhydantoin, 116 grams of hydroxyethyl acrylate, 10.09 grams of p-toluenesulfonic acid and 252 grams benzene. The mixture was refluxed until no more water was azeotroping into the Dean-Stark trap. The heat was turned off and the product was worked up by washing it with 500 ml deionized water, then twice with 500 ml of a 5% aqueous $NaHCO_3$ solution followed by an additional 500 ml deionized water wash. The benzene layer containing the product was then dried with anhydrous $MgSO_4$, treated with decolorizing carbon and the benzene was removed under vacuum. A 76% yield of the product, i.e.,

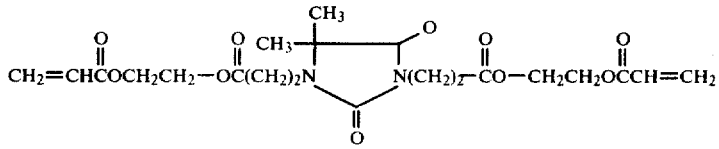

was realized.

EXAMPLE 8

1 mole of tris (2-hydroxyethyl)isocyanurate, 4.5 moles of 3-mercaptopropionic acid and 100 milliliters toluene are charged to a 1 liter three neck round bottom flask equipped with stirrer, heating mantle, thermometer and condenser Dean-Stark trap. The reaction was carried out for 7 hours at a temperature of about 130° C. during which time water was continuously removed in the Dean Stark trap. The extent of the reaction was calculated either from the amount of water removed or by titrating the acid value. The reaction mixture was poured into a separatory funnel and water was added. Washing with water was continued until the pH of the wash water was neutral. The toluene layer containing the product was filtered through magnesium sulfate and thereafter the toluene was stripped off at 70° C. under a reduced pressure of 20 mm in a rotating evaporator. The yield of the tris (3-mercaptopropionate) ester of tris (2-hydroxyethyl) isocyanurate i.e.,

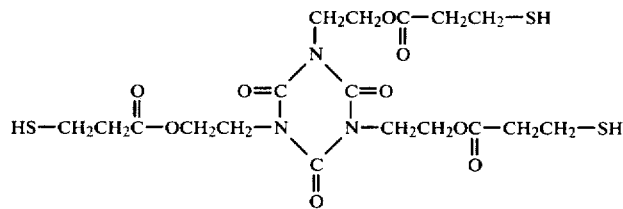

was in excess of 90%.

The following example shows the utility of the polyene of the instant invention with a polythiol in forming a cured polythioether when subjected to radiation.

When U.V. radiation is used, a photosensitizer or photocuring rate accelerator is usually added to the system along with various conventional stabilizers to extend shelf life.

EXAMPLE 9

The following formulations were made up from accurately weighed ingredients and admixed until homogeneous.

Formulation A 30.00 g. polyene 3 from Example 3
21.91 g. commercially available pentaerythritol tetrakis (β-mercaptopropionate)
1.56 g. benzophenone
0.07 g. stabilizer package

Formulation B 20.00 g. polyene 3 from Example 3
2.38 g. commercially available iso-diallylphthalate
23.66 g. commercially available tris-(3-mercaptopropionyloxyethyl)-isocyanurate
1.38 g. benzoin isopropyl ether
1.41 g. stabilizer package

Formulation C 398 g. commercially available triallyl cyanurate (C═C 11.60)
591 g. pentaerythritol tetrakis (β-mercaptopropionate)
19.8 g. benzophenone
.05 g. stabilizer package

Formulation D 70.7 g. commercially available triallylisocyanurate (C═C 12.09)
116.3 g. commercially available trimethylolpropane tris (β-mercaptopropionate)
3.7 g. benzophenone
0.4 g. stabilizer package

Formulation E 292.2 g. commercially available triallyl cyanurate (C═C 11.50)
457.8 g. commercially available trimethylolpropane tris (β-mercaptopropionate)
15.0 g. benzophenone
0.3 g. stabilizer package

Formulation F 100 g. diallyl phthalate monomer and oligomer mixture, the oligomer containing an average of 10–30 repeating units commercially available from FMC under tradename "Dapon" sealant
112.4 g. polythiol from Example 8
4.2 g. benzophenone
0.1 g. stabilizer package Each formulation was poured on a glass plate and drawn down to a 10 mil thick film. The film was exposed to U.V. radiation for 1.5 minutes under an Addalux lamp at a surface intensity of 13,400 microwatts/cm$^2$, peeled off the glass surface, and then exposed another 1.5 minutes on the reverse side of the film. The cured samples were measured for modulus, tensile strength and elongation-to-failure, and then heat aged in a forced air circulated oven at 180° C. for one week, and remeasured. The results are shown in Table I.

TABLE I

M = Modulus (10$^{-3}$), psi
T = Tensile Strength, psi

| Formulation | Control | | | 7 days at 180° C. | | | Color After Heat Aging |
|---|---|---|---|---|---|---|---|
| | M | T | E | M | T | E | |
| A | 2.6 | 542 | 25 | 195 | 2481 | 44 | Light brown |
| B | 8.6 | 620 | 82 | 170 | 1350 | 115 | Light brown |
| C | 18.1 | 1495 | 42 | 275.2 | 8257 | 5 | Brown |
| D | 127.0 | 1655 | 62 | 267.1 | 7265 | 4 | Dark brown |
| E | 2.5 | 507 | 26 | 344.9 | 8283 | 4 | Dark brown |
| F | 1.0 | 409 | 130 | 297.2 | 6142 | 3 | Brown |

As can be seen from TABLE I, the materials containing the dimethylhydantoin derived polyenes (A and B) are far more heat resistant than those formulations not containing the dimethylhydantoin polyenes. This is shown by the sharp drop in the values of elongation-to-failure of entries C-F as opposed to the values given by entries A and B.

EXAMPLE 10

A 24 AWG copper wire was passed through a degreasing bath of methylene chloride followed by drying. The wire was then passed into a bath of the liquid radiation curable composition of Formulation B from Example 9 at ambient conditions.

The coated wire was passed through the bath, through a die to insure a homogeneous thickness of 1 mil and through a surrounding bank of U.V. pulsed xenon lamps whose major spectral lines were all above 3000 Angstroms at a speed of 20 feet per second for an exposure period of 2 secs. The sunlamps were so positioned that the surface intensity on the radiation curable composition was 22,000 microwatts/cm$^2$. The resulting wire had a smooth, cured coating of 1 mil thickness and showed good flexibility and adhesion on bending.

Various wire and cable electrical conductors such as copper, aluminum and steel can be coated with the cured polythioether material of the instant invention with coating thicknesses ranging from 0.2 to 100 mils.

We claim:

1. The process of forming a solid crosslinked polythioether which comprises admixing a composition comprising (1) a polyene of the formula $$(X)_y\text{-}(A)_a\text{-}(T)\text{-}(Y)\text{-}N\underset{\underset{O}{\parallel}}{\overset{\overset{\displaystyle CH_3\ \ CH_3}{\diagdown\diagup}}{\underset{\phantom{X}}{\mathrm{C}}}}\phantom{xx}\overset{O}{\overset{\parallel}{\mathrm{C}}}\phantom{x}N\text{-}(Y)\text{-}(T)\text{-}(A)_a\text{-}(X)_y\Big]_n$$

wherein Y is alkylene containing 2 to 3 carbon atoms; T is a member of the group consisting of $$-\overset{O}{\overset{\parallel}{C}}-;\ -NH\overset{O}{\overset{\parallel}{C}}-NH-;\ -\overset{O}{\overset{\parallel}{C}}-NH-\ \text{and}\ -NH-;$$

A is a polyvalent organic radical member free of reactive carbon to carbon unsaturation and independently selected from the group consisting of aryl, substituted aryl, aralkyl, substituted aralkyl, cycloalkyl, substituted cycloalkyl, alkyl and substituted alkyl each containing up to 36 carbon atoms and mixtures thereof, said group members can be connected by a chemically compatible linkage selected from the group consisting of —O—, —S—, carboxylate, carbonate, carbonyl, urethane and substituted urethane, urea and substituted urea, amide and substituted amide, amine and substituted amine, and sulfone; said substituents on the substituted members may be such groups as chloro, bromo, nitro, acetoxy, acetamido, phenyl, benzyl, alkyl and alkoxy of 1 to 9 carbon atoms, cycoalkyl of 3 to 8 carbon atoms, X is a member selected from the group consisting of (a) —(CH$_2$)$_d$—CR'=CHR, (b) —O—(CH$_2$)$_d$—CR'—CHR, (c) —S—(CH$_2$)$_d$—CR'=CHR, (d) —(CH$_2$)$_d$—C≡CR, (e) —O—(CH$_2$)$_d$—C≡CR, (f) —S—(CH$_2$)$_d$—C≡CR;

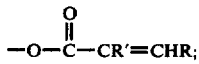  (g)

and mixtures thereof; where R and R' each are independently selected from the group consisting of hydrogen and methyl radicals; d is an integer from 0 to 1; n is 1 to 30; and y from 1 to 10; (2) a polythiol containing at least 2 thiol groups per molecule, the total combined functionality of (a) the reactive terminal unsaturated carbon to carbon bonds per molecule in the polyene and (b) the thiol groups per molecule in the polythiol being greater than 4 and (3) 0.005 to 50% by weight of said curable composition of a photocuring rate accelerator and exposing said curable composition to actinic radiation.

2. The process of coating a substrate which comprises applying to a substrate a curable composition comprising (1) a polyene of the formula:

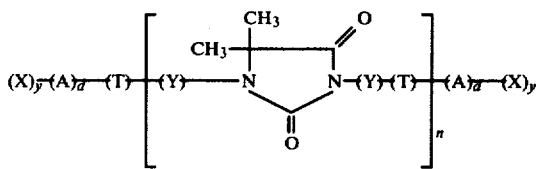

wherein Y is alkylene containing 2 to 3 carbon atoms; T is a member of the group consisting of

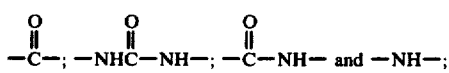

A is a polyvalent organic radical member free of reactive carbon to carbon unsaturation and independently selected from the group consisting of aryl, substituted aryl, aralkyl, substituted aralkyl, cycloalkyl, substituted cycloalkyl, alkyl and substituted alkyl each containing up to 36 carbon atoms and mixtures thereof, said group members can be connected by a chemically compatible linkage selected from the group consisting of —O—, —S—, carboxylate, carbonate, carbonyl, urethane and substituted urethane, urea and substituted urea, amide and substituted amide, amine and substituted amine, and sulfone; said substituents on the substituted members may be such groups as chloro, bromo, nitro, acetoxy, acetamido, phenyl, benzyl, alkyl and alkoxy of 1 to 9 carbon atoms, and cycloalkyl of 3 to 3 carbon atoms, X is a member selected from the group consisting of (a) —(CH$_2$)$_d$—CR'=CHR, (b) —O—(CH$_2$)$_d$—CR'—CHR, (c) —S—(CH$_2$)$_d$—CR'=CHR, (d) —(CH$_2$)$_d$—C≡CR, (e) —O—(CH$_2$)$_d$—C≡CR, (f) —S—(CH$_2$)$_d$—C≡CR;

  (g)

and mixtures thereof, where R and R' each are independently selected from the group consisting of hydrogen and methyl radicals; d is an integer from 0 to 1; n is 1 to 30; and y from 1 to 10; (2) a polythiol containing at least 2 triol groups per molecule, the total combined functionality of (a) the reaction terminal unsaturated carbon to carbon bonds per molecule in the polyene and (b) the thiol groups per molecule in the polythiol being greater than 4 and (3) 0.005 to 50% by weight of said curable composition of a photocuring rate accelerator and exposing said curable composition to actinic radiation to form a solidified, cured polythioether coating on said substrate.

* * * * *